(12) United States Patent
Kawahara

(10) Patent No.: US 11,344,182 B2
(45) Date of Patent: May 31, 2022

(54) ENDOSCOPE AND ENDOSCOPE SYSTEM

(71) Applicant: OLYMPUS CORPORATION, Tokyo (JP)

(72) Inventor: Kosuke Kawahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 155 days.

(21) Appl. No.: 16/846,832

(22) Filed: Apr. 13, 2020

(65) Prior Publication Data

US 2020/0237194 A1    Jul. 30, 2020

Related U.S. Application Data

(63) Continuation of application No. PCT/JP2017/037339, filed on Oct. 16, 2017.

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00009* (2013.01); *A61B 1/00013* (2013.01);
(Continued)

(58) Field of Classification Search
CPC ............ A61B 1/00096; A61B 1/00009; A61B 1/00013; A61B 1/00165; A61B 1/042;
(Continued)

(56) References Cited

U.S. PATENT DOCUMENTS 4,653,478 A * 3/1987 Nagasaki ................. A61B 1/05
600/109
2007/0232860 A1    10/2007 Kubo et al.
(Continued)

FOREIGN PATENT DOCUMENTS

CN    103486542    *  1/2014    ............... F21V 13/04
JP    2003177286 A  *  9/1998    ........... G02B 6/4246
(Continued)

OTHER PUBLICATIONS

International Search Report dated Jan. 9, 2018 issued in PCT/JP2017/037339.

*Primary Examiner* — Michael J Carey
*Assistant Examiner* — Amy Kristina Polanecki
(74) *Attorney, Agent, or Firm* — Scully, Scott, Murphy & Presser, P.C.

(57) ABSTRACT

An endoscope includes: an image pickup device configured to convert image pickup light into an image pickup signal and output the image pickup signal; a light emitting element configured to output an optical signal based on the image pickup signal; a bonded prism including: a first prism including a first reflecting surface configured to reflect the image pickup light and a lower surface that is a first emitting surface configured to emit the image pickup light to the image pickup device; and a second prism including a second reflecting surface configured to reflect the optical signal that is incident from an upper surface and outputted from the light emitting element, the second reflecting surface being bonded with the first reflecting surface; and an optical fiber configured to transmit the optical signal reflected by the second reflecting surface.

19 Claims, 7 Drawing Sheets

(51) Int. Cl.
*A61B 1/07* (2006.01)
*A61B 1/05* (2006.01)
*G02B 23/24* (2006.01)

(52) U.S. Cl.
CPC .......... *A61B 1/00165* (2013.01); *A61B 1/042* (2013.01); *A61B 1/07* (2013.01)

(58) Field of Classification Search
CPC .. A61B 1/07; A61B 1/051; A61B 1/05; A61B 1/00–1/32; G02B 23/24; G02B 6/42–6/43
See application file for complete search history.

(56) References Cited

U.S. PATENT DOCUMENTS

| | | |
|---|---|---|
| 2007/0286231 A1 | 12/2007 | Kubo et al. |
| 2011/0064358 A1* | 3/2011 | Nishimura ........... G02B 6/4214 385/47 |
| 2013/0266262 A1 | 10/2013 | Nishimura et al. |
| 2015/0038787 A1* | 2/2015 | Nishimura ........... A61B 1/0638 600/109 |

FOREIGN PATENT DOCUMENTS

| | | | | |
|---|---|---|---|---|
| JP | 2003-177286 A | | 6/2003 | |
| JP | 2003177286 A | * | 6/2003 | ........... G02B 6/4246 |
| JP | 2005-352256 A | | 12/2005 | |
| JP | 2006-072365 A | | 3/2006 | |
| JP | 2007-260066 A | | 10/2007 | |
| JP | 2008-011504 A | | 1/2008 | |
| JP | 2013-235243 A | | 11/2013 | |
| JP | 2014-117520 A | | 6/2014 | |
| JP | 2014-137584 A | | 7/2014 | |
| JP | 2015-024029 A | | 2/2015 | |
| JP | 2015-198726 A | | 11/2015 | |
| JP | WO 2016151670 A1 | * | 9/2016 | |
| JP | WO2016151670 A1 | * | 9/2016 | ............... G02B 6/42 |

* cited by examiner

ENDOSCOPE AND ENDOSCOPE SYSTEM

CROSS REFERENCE TO RELATED APPLICATION

This application is a continuation application of PCT/JP2017/037339 filed on Oct. 16, 2017, the entire contents of which are incorporated herein by this reference.

BACKGROUND OF THE INVENTION

1. Field of the Invention

The present invention relates to an endoscope including a horizontal image pickup apparatus, which is provided at a distal end portion of an insertion portion to pick up an object image and convert an electric image pickup signal into an optical signal, thereby outputting the optical signal, and an endoscope system including the endoscope.

2. Description of the Related Art

To display a high-quality image, an endoscope including an image pickup device having a large number of pixels has been considered. When the image pickup device having a large number of pixels is used, the amount of image signals transmitted from the image pickup device to a signal processing apparatus (processor) increases. For this reason, the insertion portion may become thick due to wiring in electric signal transmission in which an electric signal is transmitted via a metal wiring.

To make the insertion portion smaller in diameter and minimally invasive, it is preferable to perform optical signal transmission in which an optical signal instead of the electric signal is transmitted via a thin optical fiber. The optical signal transmission is performed using an E/O type optical module (electric-optical converter) that converts an electric signal into an optical signal and an O/E type optical module (optical-electric converter) that converts an optical signal into an electric signal.

For example, an image pickup apparatus is disclosed in Japanese Patent Application Laid-Open Publication No. 2014-137584 in which an electric signal outputted from an image pickup device is converted into an optical signal by a surface emitting laser (VCSEL), which is a light emitting element, and the optical signal is transmitted through an optical fiber held by a ferrule.

An endoscope is disclosed in Japanese Patent Application Laid-Open Publication No. 2015-198726 in which a horizontal image pickup apparatus is provided at a distal end portion of an insertion portion. The horizontal image pickup apparatus includes, as an essential component, a triangular prism provided on a light receiving surface of an image pickup device.

An optical component for bi-directional optical communication is disclosed in Japanese Patent Application Laid-Open Publication No. 2003-177286 in which a first optical signal outputted from a light emitting element and a second optical signal inputted to a light receiving element are combined using one prism and are guided to one optical fiber.

SUMMARY OF THE INVENTION

According to an embodiment, an endoscope includes: an image pickup optical system configured to form an object image; an image pickup device configured to convert image pickup light into an image pickup signal and output the image pickup signal; at least one light emitting element configured to output an optical signal based on the image pickup signal; a bonded prism including: a first prism including a first reflecting surface configured to reflect the image pickup light that is incident from the image pickup optical system and a lower surface that is a first emitting surface configured to emit the image pickup light to the image pickup device; and a second prism including a second reflecting surface configured to reflect the optical signal that is incident from an upper surface and outputted from the light emitting element, the second reflecting surface being bonded with the first reflecting surface; and at least one optical fiber configured to transmit the optical signal reflected by the second reflecting surface.

According to another embodiment, an endoscope includes: an image pickup optical system configured to form an object image; a prism including a first reflecting surface configured to reflect image pickup light incident from the image pickup optical system; an image pickup device configured to convert image pickup light into an image pickup signal and output the image pickup signal; a light emitting element configured to output an optical signal based on the image pickup signal; an optical fiber that extends in an extension direction of an optical axis of the image pickup optical system; a first wiring board on which the image pickup device is mounted; and a second wiring board disposed above the first reflecting surface, wherein the prism is one triangular prism, the light emitting element is mounted on the second wiring board, and the optical signal is reflected by a back surface of the first reflecting surface or a reflecting film provided on the back surface, and is guided to the optical fiber configured to transmit an optical signal.

According to further another embodiment, an endoscope system includes: an endoscope including: an image pickup optical system configured to form an object image; an image pickup device configured to convert image pickup light into an image pickup signal and output the image pickup signal; a light emitting element configured to output an optical signal based on the image pickup signal; a bonded prism including: a first prism including a first reflecting surface configured to reflect the image pickup light that is incident from the image pickup optical system and a lower surface that is a first emitting surface configured to emit the image pickup light to the image pickup device; and a second prism including a second reflecting surface configured to reflect the optical signal that is incident from an upper surface and outputted from the light emitting element, the second reflecting surface being bonded with the first reflecting surface; and an optical fiber configured to transmit the optical signal reflected by the second reflecting surface; a light source configured to generate pulse illumination light; an illumination optical system configured to emit the pulse illumination light; an optical signal control circuit configured to control a period at which the optical signal is outputted; and a timing control circuit configured to control the light source and the optical signal control circuit in a state where an irradiation period of the pulse illumination light does not overlap with an outputted period at which the optical signal is outputted.

DETAILED DESCRIPTION OF THE PREFERRED EMBODIMENTS

First Embodiment

Figure 1:
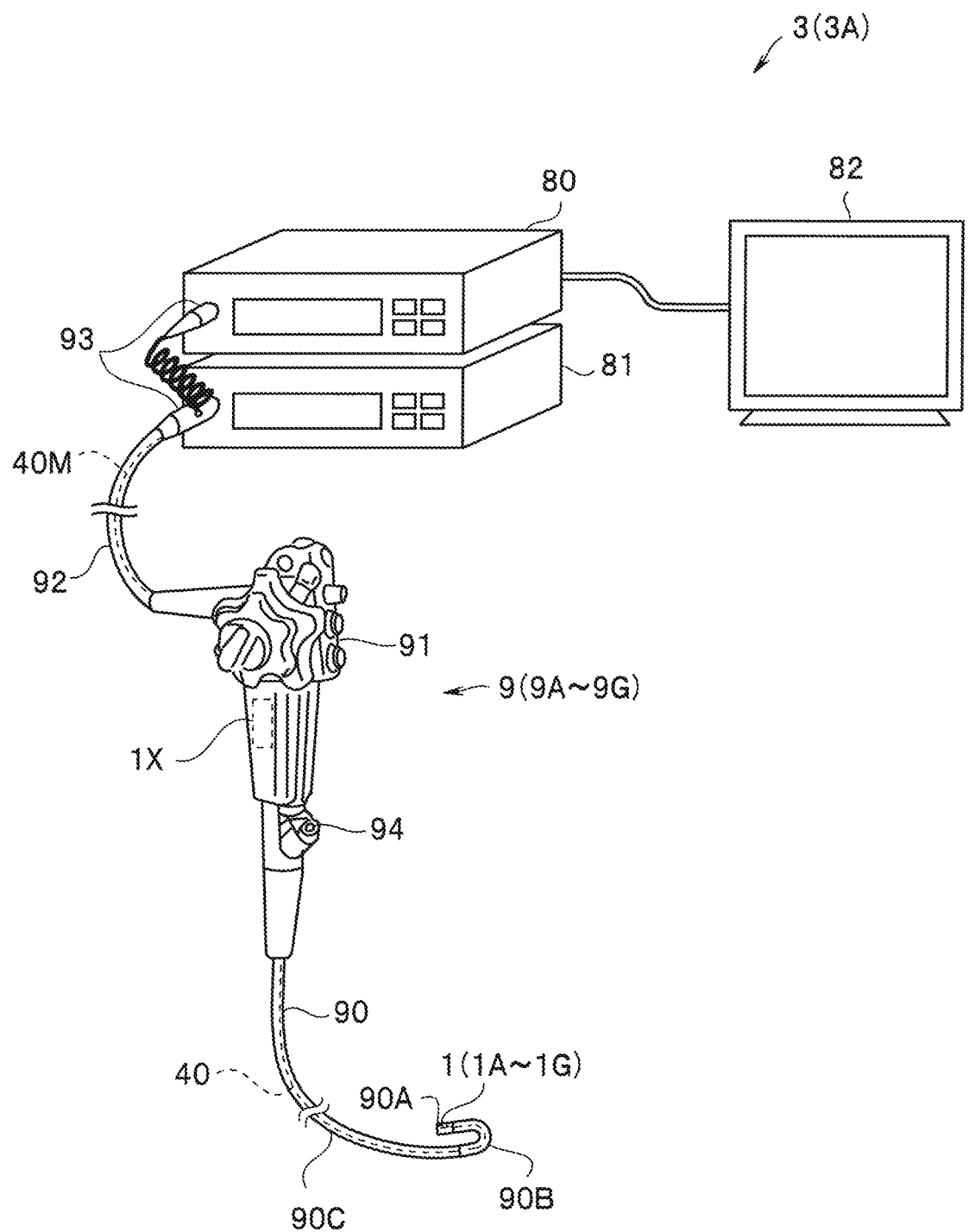
FIG. 1 is a perspective view of an endoscope according to a first embodiment.

As shown in FIG. 1, an endoscope system 3 including an endoscope 9 of the present embodiment includes the endoscope 9, a processor 80, a light source apparatus 81, and a monitor 82. For example, the endoscope 9 is configured such that a flexible insertion portion 90 is inserted into a body cavity of a subject to pick up an image of an internal body of the subject and output an image pickup signal.

An operation portion 91 including various buttons for operating the endoscope 9 is provided on a proximal end side of the insertion portion 90 of the endoscope 9. The operation portion 91 includes a treatment instrument insertion port of a channel 94 through which a living body forceps, an electrocautery, and an inspection probe are inserted into the body cavity of the subject.

The insertion portion 90 is configured by a rigid distal end portion 90A on which an image pickup apparatus 1 including an E/O type optical module is provided, a bendable bending portion 90B continuously provided on a proximal end side of the distal end portion 90A, and a flexible portion 90C continuously provided on a proximal end side of the bending portion 90B. The bending portion 90B is bent by an operation of the operation portion 91.

A universal cord 92 extending from the operation portion 91 is connected to the processor 80 and the light source apparatus 81 via a connector 93.

The processor 80 controls the entire endoscope system 3, and performs signal processing on an image pickup signal outputted from the image pickup apparatus 1 to output an image signal. The monitor 82 displays the image signal outputted from the processor 80.

The light source apparatus 81 includes, for example, a white LED. Illumination light emitted from the light source apparatus 81 is guided to an illumination optical system 96 on the distal end portion 90A via the universal cord 92 and a light guide 98 which passes through the insertion portion 90, and illuminates an object (see FIG. 12).

The image pickup apparatus 1 including an O/E type optical module generates an image pickup signal and converts the image pickup signal into an optical signal. The optical signal is transmitted to the operation portion 91 via a thin optical fiber 40 that passes through the insertion portion 90. Then, the optical signal is converted into an electric signal again by an O/E type optical module 1X provided in the operation portion 91, and is transmitted to the electric connector 93 via a signal cable 40M which is a metal wiring that passes through the universal cord 92. In other words, the image pickup signal is transmitted via the optical fiber 40 in the insertion portion 90 having a small diameter, and is transmitted via the signal cable 40M which is the metal wiring thicker than the optical fiber 40 in the universal cord 92 which is not inserted into the body and is small in restriction of an outer diameter.

When the optical module 1X is arranged in the connector 93 or the processor 80, the optical fiber 40 passes through the universal cord 92.

Figure 2:
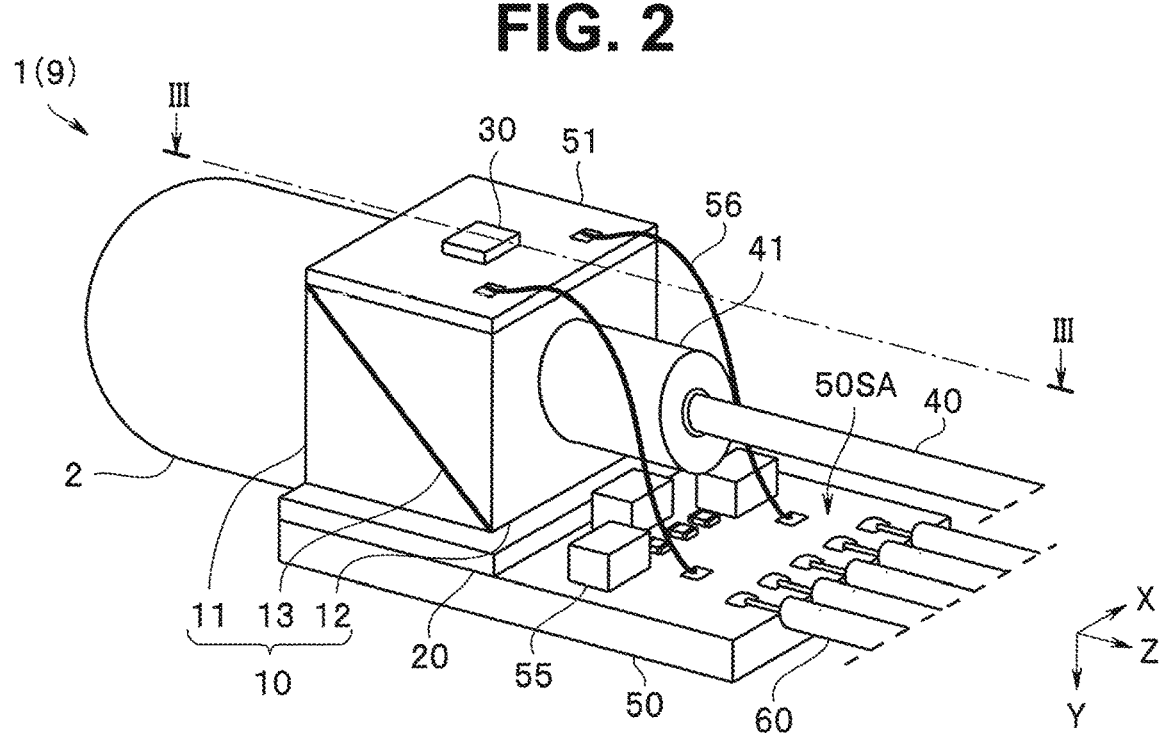
FIG. 2 is a perspective view of an image pickup apparatus of the endoscope according to the first embodiment.
Figure 3:
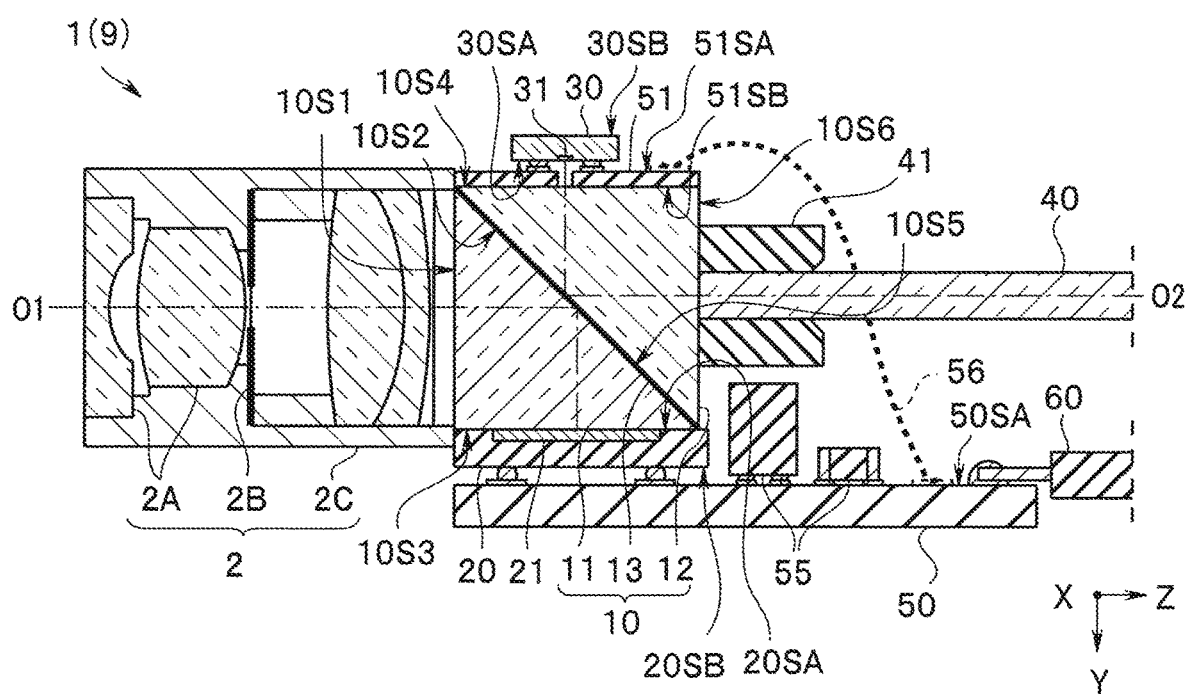
FIG. 3 is a cross-sectional view taken along line in FIG. 2 of the image pickup apparatus of the endoscope according to the first embodiment.

As shown in FIGS. 2 and 3, the image pickup apparatus 1 of the endoscope 9 according to the present embodiment includes an image pickup optical system 2, a prism 10, an image pickup device 20, a light emitting element 30, and a first wiring board 50.

In the following description, the drawings based on each embodiment are schematic. A relation between a thickness and a width of each portion, a ratio of the thickness of each portion, and a relative angle are different in reality. The drawings include portions having different dimensional relations and ratios between the drawings. Some components may not be shown. In an XYZ orthogonal coordinate system shown herein, a direction in which a Y-axis value increases, that is, a direction in which the image pickup device 20 is disposed with respect to the prism 10 is referred to as a "downward direction", and a direction in which the Y-axis value decreases is referred to as an "upward direction".

In the image pickup optical system 2 which forms an object image, a plurality of lenses 2A and an optical aperture 2B are housed in a lens barrel 2C.

The prism 10 is a bonded prism in which a first triangular prism 11 and a second triangular prism 12 are bonded by a bonding layer 13. The first triangular prism 11 includes a first incident surface 10S1 (hereinafter, also referred to as an "incident surface 10S1") on which image pickup light is incident from the image pickup optical system 2, a first reflecting surface 10S2 that reflects the image pickup light, and a first emitting surface 10S3 that emits the image pickup light. On the other hand, the second triangular prism 12 includes an upper surface 10S4 serving as a second incident surface which is orthogonal to the incident surface 10S1 and on which the optical signal is incident, a second reflecting surface 10S5 that reflects the optical signal, and a second emitting surface 10S6 that faces the incident surface 10S1 to emit the optical signal. The second reflecting surface 10S5 bonded to the first reflecting surface 10S2 by the bonding layer 13 is parallel to the first reflecting surface 10S2.

In other words, the second triangular prism 12, which reflects the optical signal, is disposed in a space (an overlapped space of a virtually extending space of the incident surface 10S1 and a virtually extending space of the emitting surface 10S3) above the first triangular prism 11 that is an essential component of a horizontal image pickup apparatus in which the image pickup device 20 is substantially parallel to an optical axis O of the image pickup optical system 2 and image pickup light is reflected by the reflecting surface and is incident on the image pickup device 20.

Since the first triangular prism 11 and the second triangular prism 12 are rectangular prisms having substantially the same size, the prism 10 having the same size of the incident surface 10S1 and the second emitting surface 10S6 has a substantially rectangular parallelepiped shape in which the upper surface 10S4 is the optical signal incident surface and a lower surface is the emitting surface 10S3 of the image pickup light.

In a field of optical communication, a bonded prism, which combines two optical signals into one optical signal or has a beam splitter function to split one optical signal into two optical signals is used. However, the first triangular prism 11 and the second triangular prism 12 of the prism 10 function independently. In other words, since the bonding layer 13 of the prism 10 is a light-shielding resin, the image pickup light incident on the first triangular prism 11 and the optical signal incident on the second triangular prism 12 do not almost interfere with each other. The bonding layer 13 may be a transparent resin as long as the first reflecting surface 10S2 and/or the second reflecting surface 10S5 are coated with a reflecting film such as aluminum or gold.

The image pickup device 20 includes a light receiving surface 20SA and a back surface 20SB facing the light receiving surface 20SA. A light receiving portion 21 is provided on the light receiving surface 20SA, and a plurality of external electrodes are provided on the back surface 20SB. The image pickup device 20 made of a semiconductor such as silicon is a CCD or a CMOS image sensor in which the light receiving portion 21 is formed using a known semiconductor manufacturing technique. The light receiving portion 21 is connected to the external electrodes via a through wiring (not shown), for example. The image pickup device 20 may be either an FSI (front side illumination) image sensor or a BSI (back side illumination) image sensor.

The emitting surface 10S3 of the prism 10 is bonded to the light receiving surface 20SA of the image pickup device 20 with an ultraviolet-curable transparent adhesive, for example. The image pickup device 20 converts the image pickup light emitted from the prism 10 into an image pickup signal which is an electric signal, and outputs the converted image pickup signal from external electrodes.

The light emitting element 30 includes a light emitting surface 30SA that is a front surface and a facing surface 30SB that faces the light emitting surface 30SA. The light emitting element 30 is a VCSEL (vertical cavity surface emitting LASER) in which a light emitting portion 31 for emitting an optical signal is formed on the light emitting surface 30SA. For example, an ultra-small light emitting element 30 having a size in plan view of 250 µm×250 µm includes, on the light emitting surface 30SA, a light emitting portion 31 having a diameter of 10 µm and an external terminal configured to supply a drive signal to the light emitting portion 31.

The optical fiber 40, which transmits the optical signal generated by the light emitting element 30, includes a core having a diameter of 50 µm and a cladding having a diameter of 125 µm and covering an outer periphery of the core.

The first wiring board 50 includes a main surface 50SA made mainly of ceramic, glass, resin, fiber reinforced resin, or silicon and provided with a plurality of wiring patterns and a plurality of electrode pads. The first wiring board 50 is a single-sided wiring board, but may be a double-sided wiring board or a multilayer wiring board.

On the main surface 50SA of the first wiring board 50, the external electrodes on the back surface 20SB of the image pickup device 20 are mounted. Note that the "mounted" means a state in which the disposed members are fixed by solder or the like and are electrically connected to each other.

On the main surface 50SA of the first wiring board 50, a plurality of electronic components 55 are also mounted. The electronic components 55 are, for example, an inductor, a capacitor, an analog/digital conversion circuit element, and a signal processing circuit element. In the image pickup apparatus 1, a drive element as one of the electronic components 55 is also mounted on the first wiring board 50 to convert the image pickup signal outputted from the image pickup device 20 into the drive signal of the light emitting element 30.

In addition, a signal cable 60 is bonded to the first wiring board 50 and is used to supply power to the image pickup apparatus 1 or transmit and receive a control signal.

The light emitting element 30 is mounted on a second wiring board 51 provided on the upper surface 10S4 of the prism 10. In other words, the second wiring board 51 is disposed above the first reflecting surface 10S2 in parallel with the emitting surface 10S3. For this reason, the light emitting surface 30SA of the light emitting element 30, the upper surface 10S4 and the emitting surface 10S3 of the prism 10, the light receiving surface 20SA of the image pickup device 20, and the main surface 50SA of the first wiring board 50 are disposed in parallel with each other.

The second wiring board 51 includes a through hole serving as an optical path of the optical signal. Further, electrode pads of the second wiring board 51 connected to the external terminals of the light emitting element 30 via wiring patterns are connected to the electrode pads of the first wiring board 50 via bonding wires 56.

On the upper surface 10S4 of the prism 10 having a function of the wiring board, the light emitting element 30 may be mounted. In other words, the external terminals of the light emitting element 30 may be bonded to the electrode pads provided on the upper surface 10S4. Further, the second wiring board 51 and the first wiring board 50 may be connected to each other by side wirings of the prism 10 or the like instead of the bonding wires 56.

The image pickup apparatus 1 further includes a ferrule 41 with the through hole into which the distal end portion of the optical fiber 40 is inserted. The ferrule 41 is provided on the second emitting surface 10S6 of the prism 10. A distal end surface of the optical fiber 40 inserted into the ferrule 41 faces the second emitting surface 10S6 of the prism 10. In order to prevent interface reflection, a gap between the distal end surface of the optical fiber 40 and the second emitting surface 10S6 is preferably filled with a transparent resin as a refractive index matching material.

In the image pickup apparatus 1, the image pickup light of the image pickup optical system around an optical axis O1 as a center is reflected by the first reflecting surface 10S2 of the prism 10 and is vertically incident on the light receiving surface 20SA of the image pickup device 20. On the other hand, the optical signal outputted from the light emitting element 30 is reflected by the second reflecting surface 10S5 parallel to the first reflecting surface 10S2 and is vertically incident on an incident end surface of the optical fiber along an optical axis O2.

The horizontal image pickup apparatus 1 of the endoscope 9 is short and small because the prism 12 configured to reflect the optical signal is disposed in a space above the prism 11 as an essential component configured to reflect the image pickup light. Since the image pickup apparatus 1 is short and small, the endoscope 9 is a minimally invasive endoscope in which the distal end portion 90A of the insertion portion 90 is short and small. Further, the prism 10 has a substantially rectangular parallelepiped shape, thereby being easy in terms of handling.

Modification of First Embodiment

Since endoscopes 9A to 9C according to a modification of the first embodiment are similar to and have the same effects as the endoscope 9, components having the same functions are denoted by the same reference numerals and a description thereof will not be presented.

Modification 1 of First Embodiment

Figure 4:
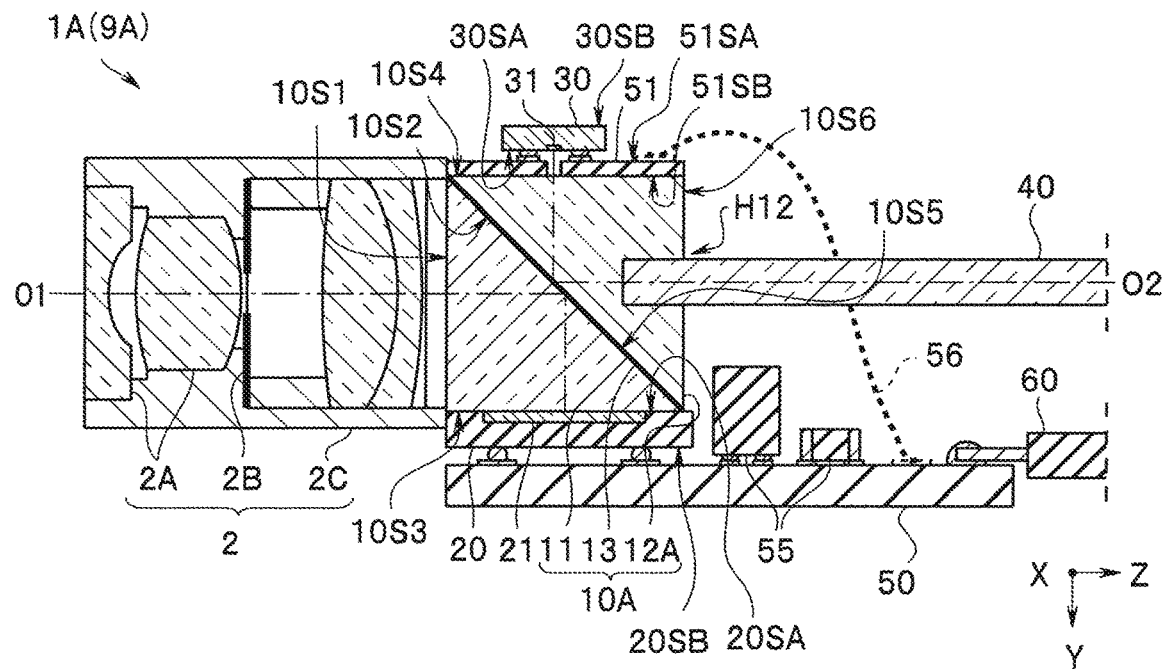
FIG. 4 is a cross-sectional view of an image pickup apparatus of an endoscope according to Modification 1 of the first embodiment.

The endoscope 9A according to Modification 1 of the first embodiment shown in FIG. 4 includes a recess H12 through which a distal end portion of an optical fiber 40 is inserted into a second emitting surface 10S6 of a prism 10A of an image pickup apparatus 1A.

Since the image pickup apparatus 1A is shorter and smaller than the image pickup apparatus 1 because of not requiring a ferrule. Therefore, the endoscope 9A is a minimally invasive endoscope including a distal end portion 90A that is shorter and smaller than that of the endoscope 9.

Modification 2 of First Embodiment

Figure 5:
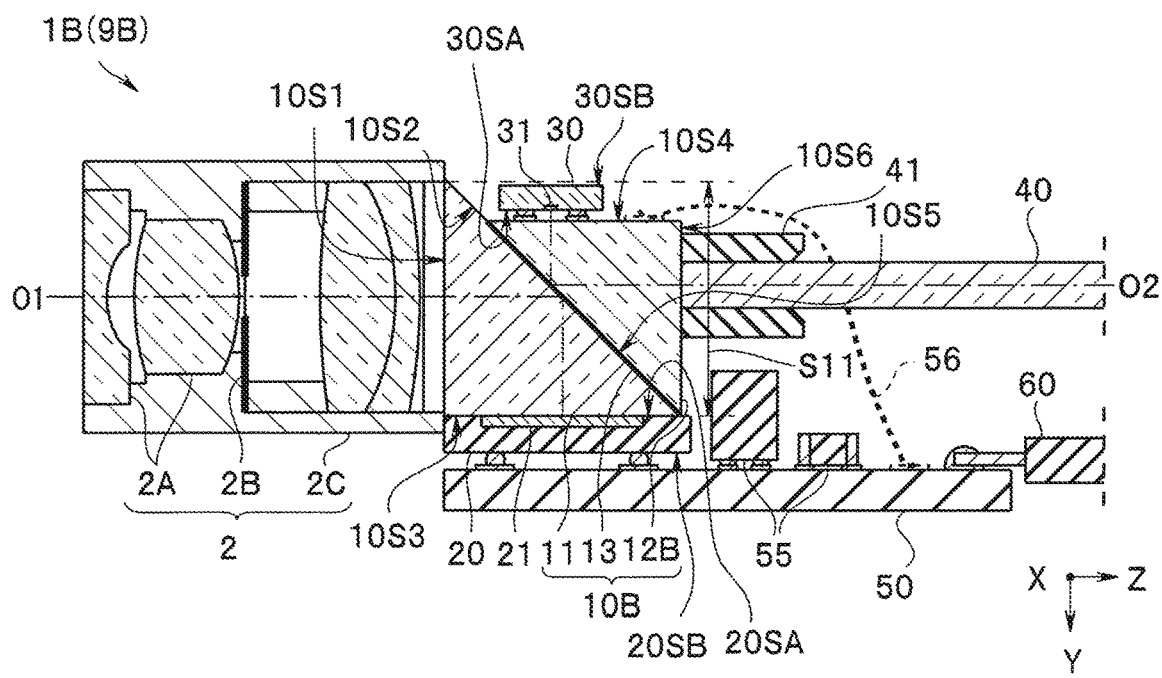
FIG. 5 is a cross-sectional view of an image pickup apparatus of an endoscope according to Modification 2 of the first embodiment.

In the endoscope 9B according to Modification 2 of the first embodiment shown in FIG. 5, a prism 10B of an image pickup apparatus 1B includes a first triangular prism 11 and a second triangular prism 12B that are different in size from each other and an incident surface 10S1 is larger than a second emitting surface 10S6.

A light emitting element 30 mounted on an upper surface 10S4 is housed in a space S11 formed by virtually extending the incident surface 10S1 in a direction of an optical axis O1 of an image pickup optical system 2.

Since the image pickup apparatus 1B is smaller in size than the image pickup apparatus 1 or the like in a direction orthogonal to the optical axis O1, the endoscope 9B includes a distal end portion 90A having a diameter smaller than that of the endoscope 9 or the like.

Further, in the image pickup apparatus 1B, the light emitting element 30 is mounted on the upper surface 10S4 of the prism 10B, and electrode pads on the upper surface 10S4 are connected to electrode pads on a first wiring board 50 via bonding wires 56.

The image pickup apparatus 1B including the prism 10B having a wiring board function does not require a second wiring board, and has a simple configuration.

Modification 3 of First Embodiment

Figure 6:
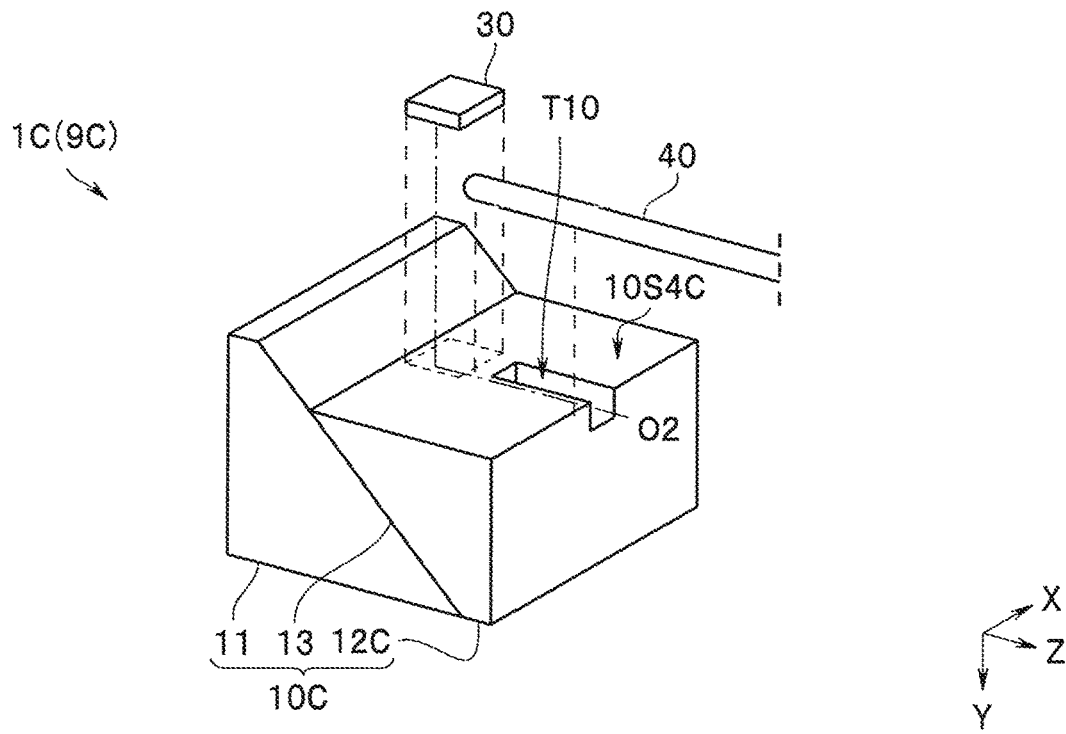
FIG. 6 is an exploded perspective view of some components of an image pickup apparatus of an endoscope according to Modification 3 of the first embodiment.

The endoscope 9B according to Modification 3 of the first embodiment shown in FIG. 6 includes a groove T10 through which a distal end portion of an optical fiber 40 is inserted into an upper surface 10S4C of a prism 10C of an image pickup apparatus 1C.

A width of the groove T10 is set to be slightly larger than an outer diameter of the optical fiber 40. Therefore, the groove T10 has the same function as a ferrule. The groove T10 has desirably a depth such that the optical fiber 40 does not protrude from the groove T10 (the optical fiber 40 fits into the groove T10), and thus the distal end portion can be made smaller in diameter.

Like the image pickup apparatus 1A, the image pickup apparatus 1C is shorter and smaller than the image pickup apparatus 1 because of not requiring a ferrule. Therefore, the endoscope 9C is a minimally invasive endoscope including a distal end portion 90A that is shorter and smaller than that of the endoscope 9.

Modification 4 of First Embodiment

Figure 7:
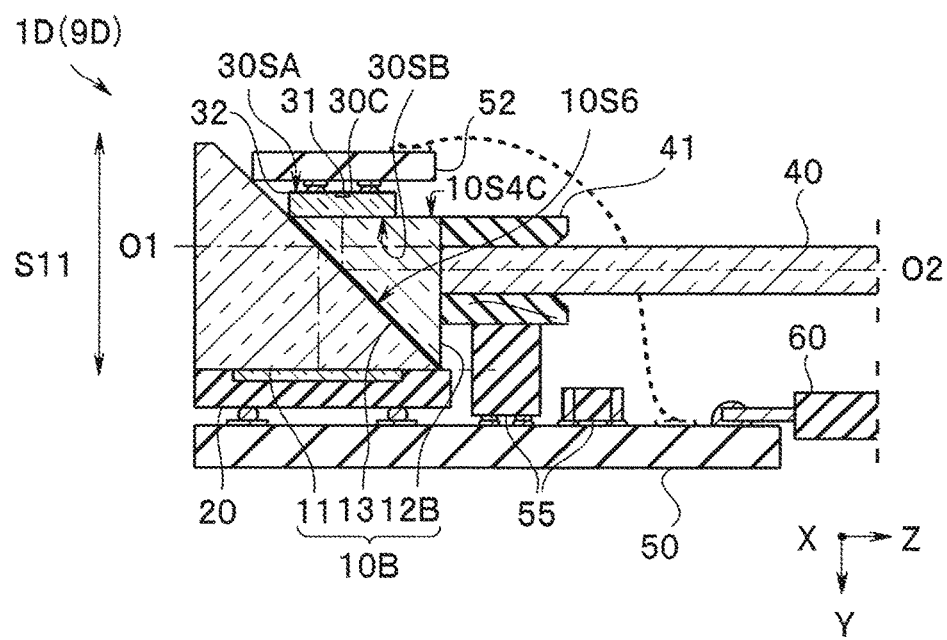
FIG. 7 is a cross-sectional view of an image pickup apparatus of an endoscope according to Modification 4 of the first embodiment.

In an endoscope 9D according to Modification 4 of the first embodiment shown in FIG. 7, a light emitting element 30C of an image pickup apparatus 1D emits an optical signal from a facing surface 30SB.

A second wiring board 52 mounted with the light emitting element 30C does not include a through hole serving as an optical path, but includes a side surface portion (not shown) to be disposed in parallel with an emitting surface 10S3.

The light emitting element 30C has a different configuration from the light emitting element 30, but since the configuration of the second wiring board is changed so as to be compatible with the light emitting element 30C, the endoscope 9D has the same effect as the endoscope 9C or the like.

Second Embodiment

Since an endoscope 9E according to a second embodiment is similar to and has the same effect as the endoscope 9, components having the same functions are denoted by the same reference numerals and a description thereof will be omitted.

Figure 8:
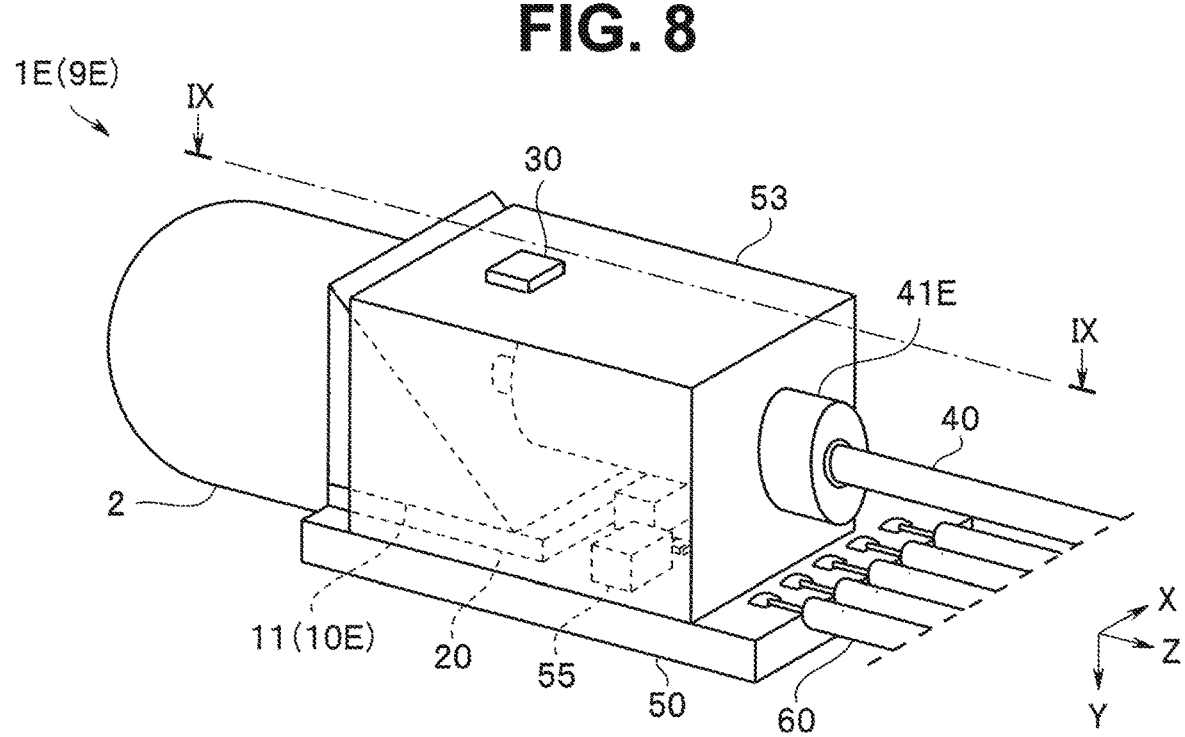
FIG. 8 is a perspective view of an image pickup apparatus of an endoscope according to a second embodiment.
Figure 9:
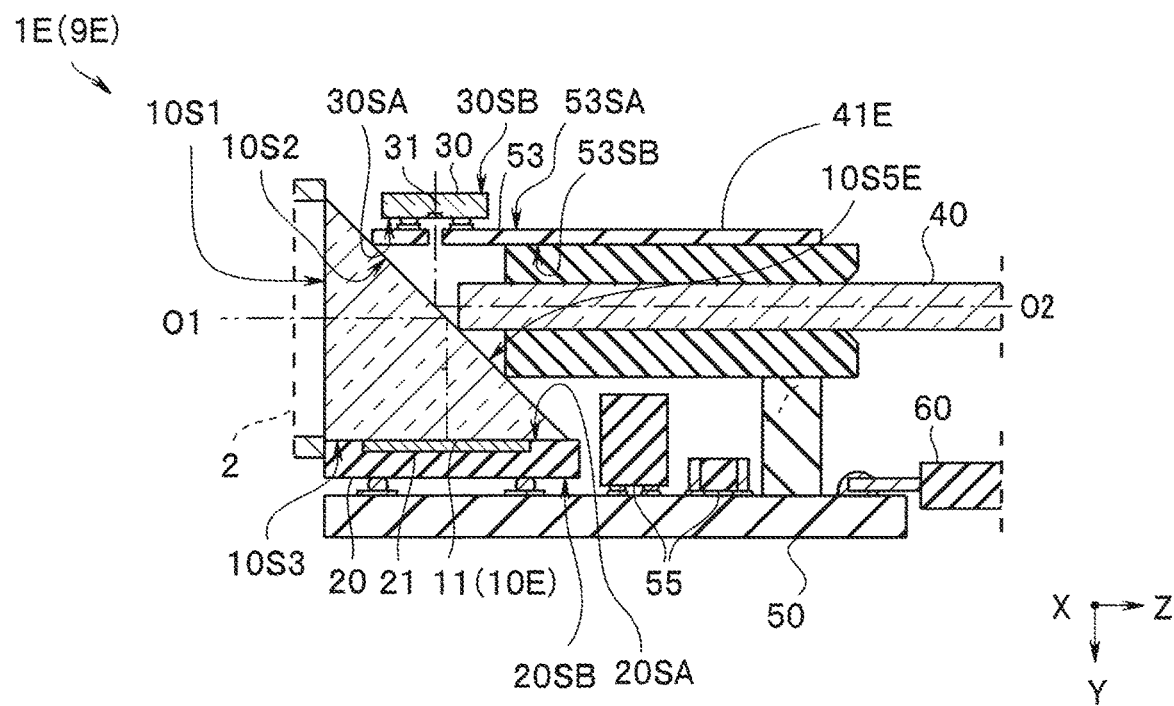
FIG. 9 is a cross-sectional view taken along line IX-IX in FIG. 8 of the image pickup apparatus of the endoscope according to the second embodiment.

As shown in FIGS. 8 and 9, a prism 10E of an image pickup apparatus 1E of the endoscope 9E includes only one triangular prism 11. In addition, the image pickup apparatus 1E includes a second wiring board 53 disposed in a space above a first reflecting surface 10S2 in parallel with an emitting surface 10S3. A light emitting element 30 is mounted on the second wiring board, and an optical signal is reflected by a back surface 10S5E of the first reflecting surface 10S2.

The second wiring board 53 includes a frame-like side surface portion to be disposed in parallel with the emitting surface 10S3. In a rear side surface portion of the second wiring board 53, a through hole is provided to pass through a ferrule 41E. The optical fiber 40 is positioned such that a distal end surface of the optical fiber 40 closely contacts with the triangular prism 11.

The prism 10E of the image pickup apparatus 1E has a simpler configuration and is less expensive than the prism 10.

The back surface 10S5E of the first reflecting surface 10S2 may be coated with a reflecting film such as aluminum or gold. In this case, the optical signal is reflected not by the back surface 10S5E but by a second reflecting surface which is a surface of the reflecting film parallel to the first reflecting surface 10S2.

Third Embodiment

Since an endoscope 9F according to a third embodiment is similar to and has the same effect as the endoscope 9, components having the same functions are denoted by the same reference numerals and a description thereof will be omitted.

Since the image pickup light has substantially the same area as the area of the light receiving portion 21, the first reflecting surface 10S2 of the prism 10 needs a large area. On the other hand, since the optical signal has a luminous flux diameter much smaller than the area of the light receiving portion 21 and, for example, is outputted from the light emitting portion 31 of the light emitting element 30 having a diameter of 10 μm, a wide reflecting surface is not required. Further, the size of the light emitting element 30 is smaller than the size of the prism 10.

Figure 10:
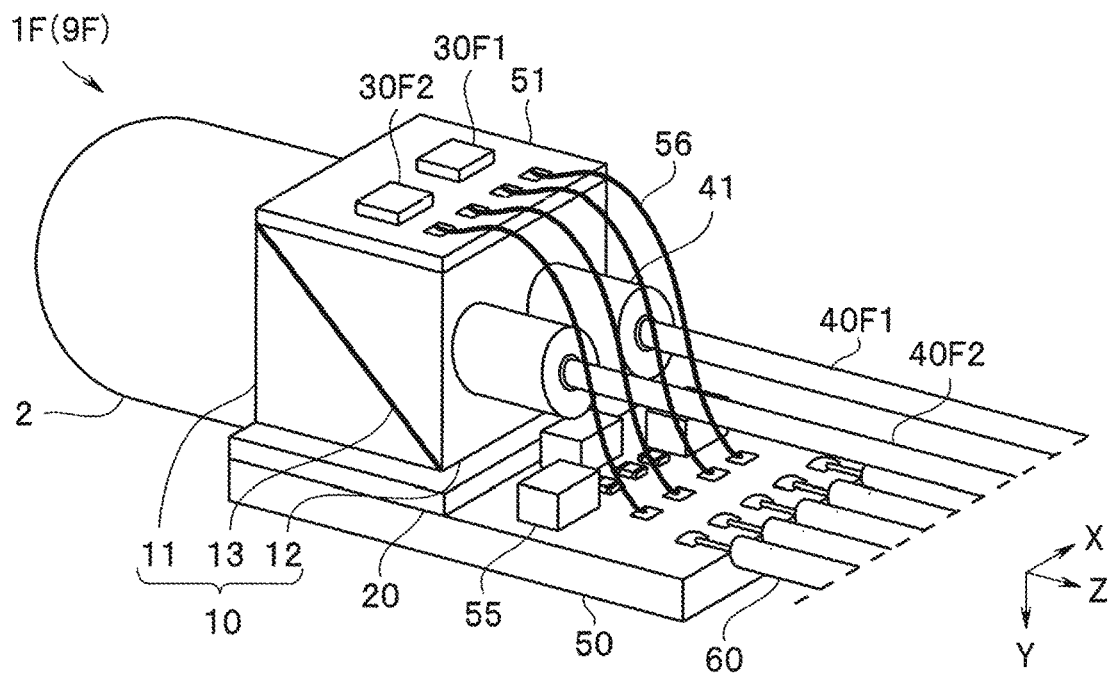
FIG. 10 is a perspective view of an image pickup apparatus of an endoscope according to a third embodiment.

Therefore, as shown in FIG. 10, an image pickup apparatus 1F of the endoscope 9F includes two light emitting elements 30F1 and 30F2 and two optical fibers 40F1 and 40F2. In other words, two optical signals are reflected by one second reflecting surface 10S5.

The image pickup apparatus may include three or more light emitting elements 30 and three or more optical fibers 40 (ferrules 41).

Figure 11:
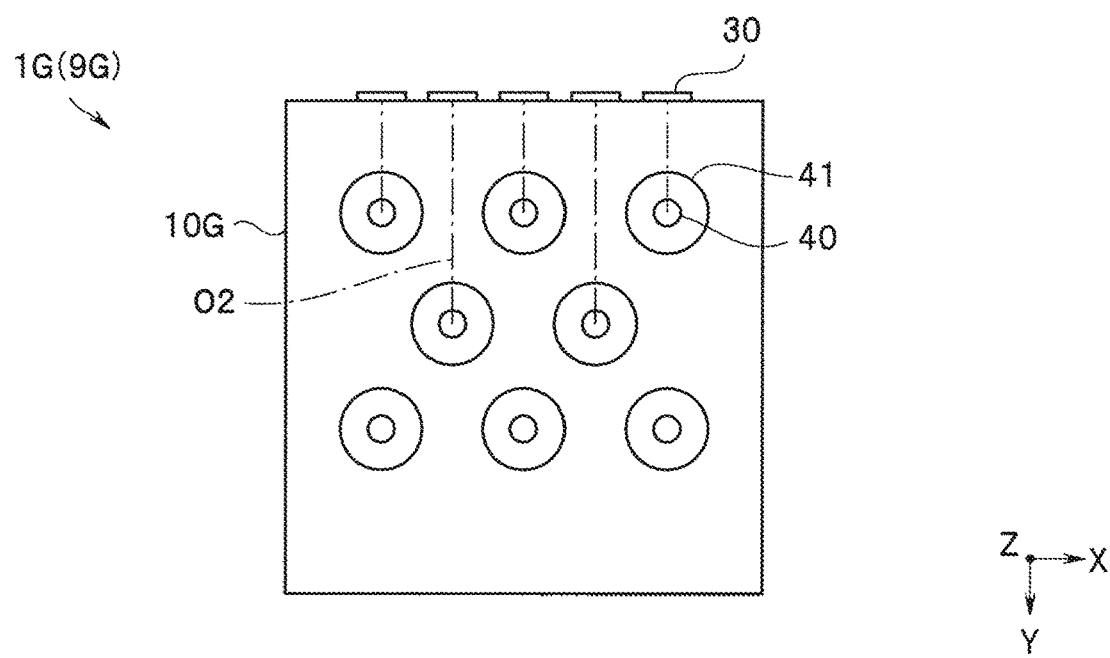
FIG. 11 is a schematic rear view of an image pickup apparatus of an endoscope according to a modification of the third embodiment.

In this case, as in the image pickup apparatus 1G of the endoscope 9G according to a modification of the third embodiment shown in FIG. 11, three or more optical fibers 40 are preferably disposed in a zigzag manner on a plane parallel to an incident surface 10S1, for example, a second emitting surface 10S6.

Fourth Embodiment

Since an endoscope system 3A according to a fourth embodiment is similar to and has the same effect as the endoscope system 3, components having the same functions are denoted by the same reference numerals and a description thereof will be omitted.

Figure 12:
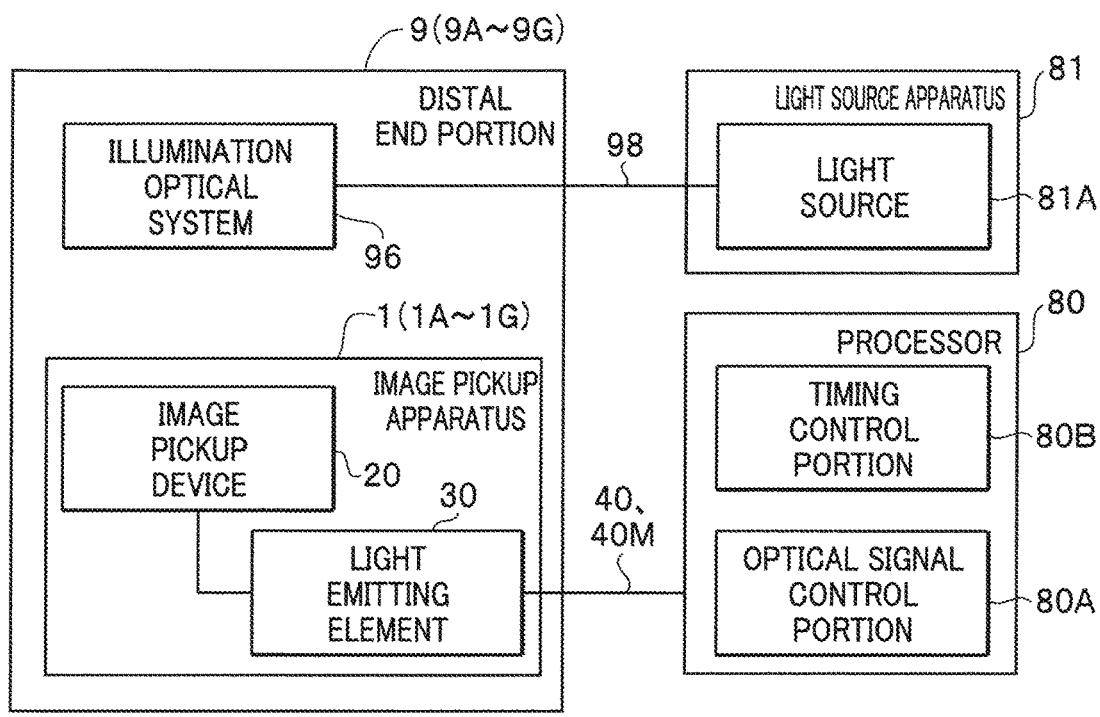
FIG. 12 is a configuration diagram of an endoscope system including an endoscope according to a fourth embodiment.

As shown in FIG. 12, the endoscope system 3A includes an endoscope 9, a light source 81A, an illumination optical system 96, an optical signal control portion 80A, and a timing control portion 80B. The light source 81A of the light source apparatus 81 generates pulse illumination light that repeats irradiation and non-irradiation. For example, the light source 81A does not generate irradiation light for 1/60 seconds after generating irradiation light for 1/60 seconds. In other words, the light source 81A generates pulse illumination light that emits light once every 1/30 seconds and repeats irradiation and non-irradiation. An illumination optical system 96 provided at a distal end portion 90A of an insertion portion 90 emits the pulse illumination light generated by the light source 81A.

On the other hand, for example, the optical signal control portion 80A of a processor 80 controls a period at which the light emitting element 30 outputs an optical signal. Then, the timing control portion 80B controls the light source 81A and the optical signal control portion 80A so that an irradiation period of the pulse illumination light does not overlap with an outputted period at which the light emitting element 30 outputs the optical signal.

Figure 13:
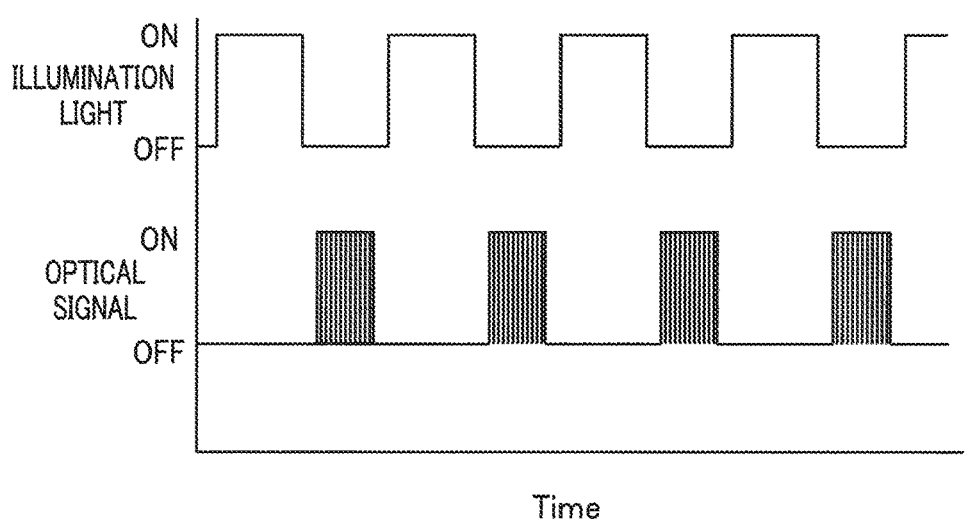
FIG. 13 is a diagram showing signal generating timing of the endoscope according to the fourth embodiment.

In other words, as shown in FIG. 13, during the irradiation period (ON) at which the light source 81A emits the illumination light, no optical signal is outputted (OFF). During the non-irradiation period (OFF) at which the light source 81A does not emit the illumination light, an optical signal is outputted (ON).

In the bonded prism 10, as described above, interfere between the image pickup light incident on the first triangular prism 11 and the optical signal incident on the second triangular prism 12 does not almost occur, but may slightly occur. In the prism 10E, the image pickup light and the optical signal may interfere with each other.

However, according to the endoscope of the present embodiment, since the light emitting element outputs the optical signal during the period at which the pulse illumination light is not irradiated, the image pickup light and the optical signal may not interfere with each other.

Note that the optical signal control portion 80A and the timing control portion 80B may be separate circuits (CPU), one circuit (CPU), or a part of the circuit (CPU) of the processor 80. Further, the optical signal control portion 80A and the timing control portion 80B may be components of the endoscope.

The endoscope 9 is a flexible endoscope including the flexible insertion portion, but may be a rigid endoscope, a medical endoscope, or an industrial endoscope.

The present invention is not limited to the above-described embodiments, and various changes, combinations, and applications can be made without departing from the scope of the invention.

What is claimed is:

1. An endoscope comprising:
   a bonded prism having a first prism bonded to a second prism along respective first and second reflecting surfaces, the bonded prism having a first side and a second side forming a first pair of opposing sides, the first side having a first incident surface and the second side having a first emitting surface, the bonded prism having a third side and a fourth side forming a second pair of opposing sides, the third side having a second incident surface and the fourth side having a second emitting surface;
   an image optical system having one or more lenses configured to form an object image, the image optical system being arranged on the first side of the first pair of opposing sides such that image light from the object image is incident on the first incident surface;
   an image sensor configured to convert image light into an image signal and output the image signal, the image sensor being arranged on the fourth side of the second pair of opposing surfaces such that the image light is reflected by the first reflecting surface, emitted from the second emitting surface and onto the image sensor;
   at least one light source configured to output an optical signal based on the image signal, the at least one light source being arranged on the third side of the second pair of opposing sides such that the optical signal is incident on the second incident surface; and
   at least one optical fiber configured to transmit the optical signal, the at least one optical fiber being arranged on the second side of the first pair of opposing sides such that the optical signal is reflected by the second reflecting surface, emitted from the first emitting surface and transmitted by the at least one optical fiber.

2. The endoscope according to claim 1, wherein the at least one light source is mounted on the second incident surface or on a wiring board provided on the second incident surface.

3. The endoscope according to claim 2, wherein the first prism and the second prism are equal in size to each other, and the bonded prism has a substantially rectangular parallelepiped shape.

4. The endoscope according to claim 2, wherein
   a first size of the first prism and a second size of the second prism of the bonded prism are different from each other, the first incident surface of the first prism on which the image light is incident is larger than the first emitting surface of the second prism from which the optical signal is emitted, and the at least one light source is housed in a space formed by projecting the first incident surface in a direction of an optical axis of the image optical system.

5. The endoscope according to claim 4, further comprising:
a ferrule including a through hole into which a distal end portion of the at least one optical fiber is inserted, wherein
the ferrule is provided on the first emitting surface.

6. The endoscope according to claim 4, wherein the first emitting surface is provided with a recess into which a distal end portion of the at least one optical fiber is inserted.

7. The endoscope according to claim 2, wherein the first emitting surface is provided with a groove into which a distal end portion of the at least one optical fiber is inserted, the groove being open to the second incident surface.

8. The endoscope according to claim 1, wherein the at least one light source comprises a plurality of light sources and the at least one optical fiber comprises a plurality of optical fibers.

9. The endoscope according to claim 8, wherein
the plurality of light sources comprises three or more light sources, and the plurality of optical fibers comprises three or more optical fibers, and
the three or more optical fibers are disposed on a plane parallel to the first incident surface.

10. The endoscope according to claim 1, wherein
the object image is light reflected from an object illuminated by pulse illumination light that repeats irradiation and non-irradiation, and
the at least one light source is configured to output the optical signal during a non-irradiation period of the pulse illumination light.

11. An endoscope system comprising:
a first light source configured to generate pulse illumination light;
an endoscope comprising:
a bonded prism having a first prism bonded to a second prism along respective first and second reflecting surfaces, the bonded prism having a first side and a second side forming a first pair of opposing sides, the first side having a first incident surface and the second side having a first emitting surface, the bonded prism having a third side and a fourth side forming a second pair of opposing sides, the third side having a second incident surface and the fourth side having a second emitting surface;
an image optical system having one or more lenses configured to form an object image, the image optical system being arranged on the first side of the first pair of opposing sides such that image light from the object image is incident on the first incident surface;
an image sensor configured to convert image light into an image signal and output the image signal, the image sensor being arranged on the fourth side of the second pair of opposing surfaces such that the image light is reflected by the first reflecting surface, emitted from the second emitting surface and onto the image sensor;
a second light source configured to output an optical signal based on the image signal, the second light source being arranged on the third side of the second pair of opposing sides such that the optical signal is incident on the second incident surface; and
an illumination optical system configured to emit the pulse illumination light; and a processor comprising hardware, the processor being configured to:
control a period at which the optical signal is outputted; and
control the first light source and the period at which the optical signal is outputted such that an irradiation period of the pulse illumination light does not overlap with an outputted period at which the optical signal is outputted.

12. An image pickup apparatus comprising:
a bonded prism having a first prism bonded to a second prism along respective first and second reflecting surfaces, the bonded prism having a first side and a second side forming a first pair of opposing sides, the first side having a first incident surface and the second side having a first emitting surface, the bonded prism having a third side and a fourth side forming a second pair of opposing sides, the third side having a second incident surface and the fourth side having a second emitting surface;
an image optical system having one or more lenses configured to form an object image, the image optical system being arranged on the first side of the first pair of opposing sides such that image light from the object image is incident on the first incident surface;
an image sensor configured to convert image light into an image signal and output the image signal, the image sensor being arranged on the fourth side of the second pair of opposing surfaces such that the image light is reflected by the first reflecting surface, emitted from the second emitting surface and onto the image sensor;
at least one light source configured to output an optical signal based on the image signal, the at least one light source being arranged on the third side of the second pair of opposing sides such that the optical signal is incident on the second incident surface; and
at least one optical fiber configured to transmit the optical signal, the at least one optical fiber being arranged on the second side of the first pair of opposing sides such that the optical signal is reflected by the second reflecting surface, emitted from the first emitting surface and transmitted by the at least one optical fiber.

13. The image pickup apparatus according to claim 12, wherein the at least one light source is mounted on the second incident surface or on a wiring board provided on the second incident surface.

14. The image pickup apparatus according to claim 13, wherein the first prism and the second prism are equal in size to each other, and the bonded prism has a substantially rectangular parallelepiped shape.

15. The image pickup apparatus according to claim 13, wherein
a first size of the first prism and a second size of the second prism of the bonded prism are different from each other, the first incident surface of the first prism on which the image light is incident is larger than the first emitting surface of the second prism from which the optical signal is emitted, and
the at least one light source is housed in a space formed by projecting the first incident surface in a direction of an optical axis of the image optical system.

16. The image pickup apparatus according to claim 15, further comprising:
a ferrule including a through hole into which a distal end portion of the at least one optical fiber is inserted, wherein
the ferrule is provided on the first emitting surface.

17. The image pickup apparatus according to claim 15, wherein the first emitting surface is provided with a recess into which a distal end portion of the at least one optical fiber is inserted.

18. The image pickup apparatus according to claim 13, wherein the first emitting surface is provided with a groove into which a distal end portion of the at least one optical fiber is inserted, the groove being open to the second incident surface.

19. The image pickup apparatus according to claim 1, wherein the at least one light source comprises a plurality of light sources and the at least one optical fiber comprises a plurality of optical fibers.

* * * * *